United States Patent
Wong et al.

(10) Patent No.: US 7,494,671 B2
(45) Date of Patent: Feb. 24, 2009

(54) **EXTRACT OF *TRAPA NATANS* AND METHODS OF USING THE SAME**

(75) Inventors: Kin-Ping Wong, 1757 Quincy Ave., Fresno, CA (US) 93720; Ming-Chung Wong, Fresno, CA (US)

(73) Assignee: Kin-Ping Wong, Fresno, CA (US)

(*) Notice: Subject to any disclaimer, the term of this patent is extended or adjusted under 35 U.S.C. 154(b) by 26 days.

(21) Appl. No.: 11/123,150

(22) Filed: May 6, 2005

(65) Prior Publication Data

US 2005/0281894 A1 Dec. 22, 2005

Related U.S. Application Data

(63) Continuation-in-part of application No. PCT/US2003/032749, filed on Nov. 10, 2003.

(60) Provisional application No. 60/425,143, filed on Nov. 8, 2002.

(51) Int. Cl.
*A61K 36/00* (2006.01)
(52) U.S. Cl. ...................................... 424/725
(58) Field of Classification Search ........................ None
See application file for complete search history.

(56) References Cited

U.S. PATENT DOCUMENTS

2005/0106667 A1* 5/2005 Fellouse et al. ............ 435/69.1
2006/0093601 A1* 5/2006 Fong et al. ................ 424/133.1

FOREIGN PATENT DOCUMENTS

CN 1091925 A * 9/1994
JP 60-064983 4/1985

OTHER PUBLICATIONS

Kumar et al, Tumour-Induced Angiogenesis: a Novel Target for Drug Therapy, Emerging Drugs (1997), vol. 2, pp. 175-190.*
USDA Plants Profile, website: http://plants.usda.gov.*

* cited by examiner

*Primary Examiner*—Christopher R Tate
*Assistant Examiner*—Deborah A. Davis
(74) *Attorney, Agent, or Firm*—King-Lit Wong

(57) ABSTRACT

The present invention provides extracts of *Trapa natans L.* useful for inhibiting, interfering and/or controlling pathological angiogenesis or neovascularization of tissues. The invention also provides a method to inhibit metastatis of cancer of colon, lung, liver, kidney, breast and/or cervix in a subject, comprising administering an effective amount of an extract of *Trapa natans L.* to the subject.

27 Claims, 1 Drawing Sheet

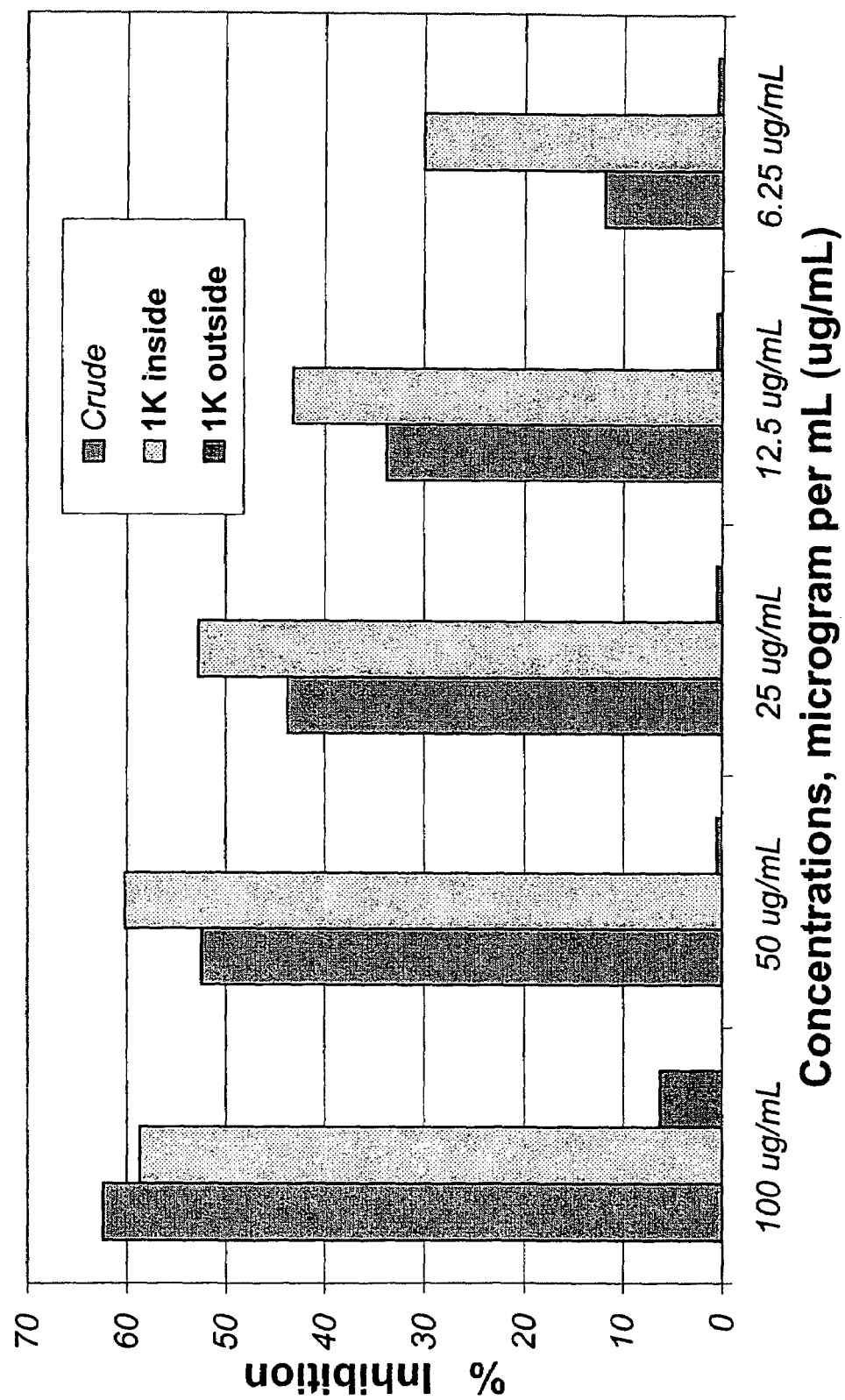

EXTRACT OF *TRAPA NATANS* AND METHODS OF USING THE SAME

This is a continuation-in-part application of PCT/US2003/032749 filed Nov. 10, 2003, which claims the priority of U.S. Provisional Application No. 60/425,143 filed Nov. 8, 2002. The disclosure of PCT/US2003/032749 is herein incorporated by reference.

FIELD OF THE INVENTION

The present invention concerns novel therapeutic interventions of pathological formation of new blood vessels and cancer metastasis. In particular, it is related to extracts of *Trapa natans L.* having anti-angiogenic properties useful for the prevention and/or treatment of cancer metastasis and health disorders associated with pathological angiogenesis and neovascularization.

BACKGROUND

*Trapa natans L.* is an aquatic plant belonging to the family Trapaceae, the water nut family. The fruit of *Trapa natans L.* is known as *Fructus Trapae*, commonly known as water caltrop, European water chestnut, water chestnut, bull nut and Jesus nut. There are two varieties of *Trapa natans L.*: two-horned trapae, *Trapa bicornis Osbeck* or *Trapa bispinosa Roxb.*, and the four-horned trapae, *Trapa quadrispinosa R.*

Angiogenesis is a process through which new blood vessels arise by outgrowth from pre-existing blood vessels. In this process, endothelial cells become detached from the basement membrane as proteolytic enzymes degrade this support. These endothelial cells then migrate out from the parent vessel, divide, and form a newly differentiated vascular structure (Risau, (1997) Nature 386:671-674; Wilting et al., (1995) Cell. Mol. Biol. Res. 41(4): 219-232). A variety of different biological factors have been found to function in controlling blood vessel formation (Bussolino et al., (1997) Trends in Biochem. Sci. 22(7): 251-256; Folkman and D'Amore, (1996) Cell 87:1153-1155). These include proteins with diverse functions such as growth factors, cell surface receptors, proteases, protease inhibitors, and extracellular matrix proteins (Achen and Stacker, (1998) Int. J. Exp. Pathol. 79:255-265; Devalaraja and Richmond, (1999) Trends in Pharmacol. Sci. 20(4): 151-156; Hanahan, (1997) Science 277:48-50; Maisonpierre et al, (1997) Science 277: 55-60; Suri et al, (1996) Cell 87:1171-1180; Sato et al, (1995) Nature 376:70-74; Mignatti and Rifkin, (1996) Enzyme Protein 49:117-137; Pintucci et al., (1996) Semin Thromb Hemost 22(6) 517-524; Vernon and Sage, (1995) Am. J. Pathol. 147(4): 873-883; Brooks et al., (1994) Science 264: 569-571; Koch et al., (1995) Nature 376:517-519).

Angiogenesis participates in essential physiological events, such as development, reproduction and wound healing. Under normal conditions, angiogenesis occurs in a carefully controlled or highly regulated manner during embryonic development, during growth, and in special cases such as wound healing and the female reproductive cycle (Wilting and Christ, (1996) Naturwissenschaften 83:153-164; Goodger and Rogers, (1995) Microcirculation 2:329-343; Augustin et al., (1995) Am. J. Pathol. 147(2): 339-351).

However, many diseases or health disorders, e.g. cancer metastasis, diabetic retinopathy, rheumatoid arthritis and other inflammatory diseases such as psoriasis, are driven by persistent unregulated angiogenesis (Folkman, (1995) Nature Med. 1(1): 27-31; Polverini, (1995) Rheumatology 38(2): 103-112; Healy et al., (1998) Hum. Reprod. Update 4(5): 736-396). For instance, in rheumatoid arthritis, new capillary blood vessels invade the joints and destroy the cartilage. In diabetic retinopathy, new capillaries in the retina invade the vitreous, bleed, and cause blindness. Therefore, effective therapeutic intervention, control and/or inhibition of pathological angiogenesis can alleviate a significant number of diseases.

The angiogenic process provides points for therapeutic intervention to control vascular formation in vivo. Protein inhibitors of angiogenesis such as angiostatin (O'Reilly et al., (1994) Cell 79(2): 315-328) and endostatin (O'Reilly et al., (1997) Cell 88(2): 277-285), that control vascular formation in experimental models, have been discovered. Nevertheless, such protein therapeutics are expensive to produce and have been found to be difficult to formulate and deliver in subjects. At present, protein angiogenesis inhibitors have yet to be developed into pharmaceuticals for patient therapy. Thus, there exists a need for therapeutic substances that can be safely administered to a patient and be effective at inhibiting, interfering, modifying and/or controlling the pathological growth of vascular endothelial cells. The present invention provides compositions and methods that are useful for this purpose.

SUMMARY OF THE INVENTION

According to the present invention, extracts of *Trapa natans L.* have been found to inhibit cancer metastasis, growth and proliferation of endothelial cells and the process of vascularization. The present invention provides a method for inhibiting, modifying and/or controlling the pathological proliferation of endothelial cells, comprising delivering to the endothelial cells an effective amount of an extract of *Trapa natans L.* Within the scope of the invention is a method to inhibit neovascularization in a tissue, comprising delivering to the tissue an effective amount of an extract of *Trapa natans L.*

The method for inhibiting, modifying and/or controlling the pathological proliferation of endothelial cells, and the method for inhibiting neovascularization in a tissue can be practiced by administering an effective amount of an extract of *Trapa natans L.* to a subject. Each of these methods optionally further comprises the application of an anti-angiogenic, anti-neovascularization or anti-tumor therapeutic regimen to the subject, wherein the extract of *Trapa natans L.* increases the therapeutic effect of the anti-angiogenic, anti-neovascularization or anti-tumor therapeutic regimen. The anti-angiogenic, anti-neovascularization or anti-tumor therapeutic regimen comprises (a) administering an anti-angiogenic or anti-neovascularization agent, e.g. Avastin (bevacizumab), ammonium sulfate precipitate of shark cartilage, extracts of shark cartilage such as AE-941 (Neovastat), Shimeji DEAE alpha, Shimeji Mono-Q alpha, 3-aminobenzamide, cisplatin, dalteparin, suramin, 2-methoxyestradiol, thalidomide, combretastain A4 phosphate, soy isoflavone (genistein, a soy protein isolate), interferon-alpha, VEGF-Trap, celecoxib, halofuginone hydrobromide and interleukin-12, other than the extract of *Trapa natans L.* to the subject, (b) administering an anti-tumor chemotherapeutic agent to the subject, wherein examples of the anti-tumor chemotherapeutic agent include, but are not limited to, doxorubicin, daunorubicin, epirubicin, paclitaxel, docetaxel, 5-fluorouracil, cyclophosphamide, methotrexate, cisplatin, carboplatin, vincristine, vinblastine, etoposide, tenoposide, bleomycin, plicamycin, mitomycin, mitotane, tamoxifen, letrozole, anastrozole, exemestane, vinorelbine, gemcitabine and capecitabine, or (c) applying radiation therapy to the subject.

Also provided herein is a method for treating a disease or disorder associated with pathological proliferation of endothelial cells and/or neovascularization by administering to a subject an effective amount of an extract of *Trapa natans L.* Optionally, the method further comprises applying the anti-tumor, anti-angiogenic or anti-neovascularization therapeutic regimen to the subject, which therapeutic regimen can comprise a regimen of chemotherapy, radiation therapy or administration of an anti-angiogenic or anti-neovascularization agent, including the examples described above, other than the extract of *Trapa natans L.* The extract of *Trapa natans L.* can enhance the therapeutic benefit of the anti-tumor, anti-angiogenic or anti-neovascularization therapeutic regimen.

The invention also provides a method for preventing or inhibiting cancer metastasis, comprising administering an effective amount of an extract of *Trapa natans L.* to a subject having cancer, preferably solid cancer of the colon, lung, liver, kidney, breast and/or cervix.

One of the objects of the invention is a method for inhibiting the pathological growth of endothelial cells, comprising delivering to the endothelial cells in vivo a growth inhibitory amount of a product comprising an extract of *Trapa natans L.* by administering a therapeutically effective amount of the product to a subject, wherein the subject has cancer, preferably solid cancer of the colon, lung, liver, kidney, breast and/or cervix, and wherein metastasis of the cancer is inhibited (i.e., stopped, reduced, slowed or delayed), and wherein the subject preferably is a mammal such as a human, pet or farm animal.

Within the scope of the invention are kits containing an effective amount of an extract of *Trapa natans L.* and instructions of using the extract in therapy. These kits are useful for treating patients having a disease associated with hyperproliferation of endothelial cells and/or neovascularization.

Further provided is a screen for identifying new therapeutic agents that have the same, similar or better therapeutic effect as an extract of *Trapa natans L.* The screen comprises comparing the effect of the agent on endothelial proliferation with the antiproliferative effect of the extract of *Trapa natans L.*

BRIEF DESCRIPTION OF THE DRAWINGS

FIG. 1 shows concentration dependant inhibition of endothelial cell proliferation by an aqueous extract of *Trapa natans L.* or dialyzed aqueous extract of *Trapa natans L.* in an Endothelial Cell Assay. In FIG. 1, the three bars at each concentration represent, from left to right, the aqueous extract of *Trapa natans L.* ("Crude"), the aqueous extract of *Trapa natans L.* after dialysis with a dialysis tubing with a cutoff of 1000 M.W. ("1K inside") and a liquid outside the dialysis tubing ("1K outside").

DETAILED DESCRIPTION OF THE INVENTION

As used in the specification and claims, the singular form "a," "an" or "the" includes plural references unless the context clearly dictates otherwise. For example, the term "a cell" includes a plurality of cells, including mixtures thereof.

The invention also provides a product comprising an extract of *Trapa natans L.* of the invention, where the methods of the invention can be practiced using the product instead of the extract alone. As used herein, when the transition term "comprising" refers to a method, substance or composition of the invention, the method, substance or composition includes the recited element(s), but not excluding any non-recited element(s).

The invention also provides a product consisting essentially of an extract of *Trapa natans L.* of the invention, where the methods of the invention can be practiced using the product instead of the extract alone. The transition phrase "consisting essentially of" when used to define a composition, substance or method of the invention in the patent application means the inclusion of the recited element(s), but not the exclusion of any non-recited elements that do not materially affect the basic and novel properties of the invention. Thus, a claimed composition consisting essentially of an extract of *Trapa natans L.* and a pharmaceutically acceptable carrier would not exclude trace contaminants from the preparation steps, e.g. isolation or purification, of the extract and substances such as phosphate buffered saline, preservatives and sodium chloride which do not materially affect the pathological angiogenesis inhibitory properties of the composition.

The term "isolated" as referring to a natural substance means that the natural substance is separated from constituents, cellular and otherwise, in which the substance is normally associated with in nature.

A "subject" or "host" is a vertebrate, preferably a mammal, more preferably a human such as a human patient. Mammals include, but are not limited to, murines, simians, equines, bovines, swines, sheep, farm animals, sport animals, pets and humans, such as human patients.

The terms, "tumor" and "neoplasm", used interchangeably and in either the singular or plural form refer to abnormal growth of cells that usually creates a tissue mass, which may be either benign or malignant.

The term "cancer", used in either the singular or plural form, refers to a mass of cells that have undergone malignant transformation. The definition of a cancer cell, as used herein, includes not only a primary cancer cell, but also any cell derived from a cancer cell ancestor. Therefore, the term "cancer cell" includes metastasized cancer cells, and in vitro cultures and cell lines derived from cancer cells. Examples of "cancer" include solid cancer of the colon, lung, liver, kidney, brain, skin, pancreas, prostate, testis, breast, ovary, uterus, cervix, head and neck.

As used herein, to "inhibit" endothelial cell growth or vascularization of a tissue means to stop, delay or slow the growth, proliferation or cell division of endothelial cells or the formation of blood vessels in the tissue. Methods to monitor inhibition include, but are not limited to, endothelial cell proliferation assays, measurement of the volume of a vascular bed by determination of blood content and quantitative determination of the density of vascular structures. When a culture is a mixture of cells, neovascularization is monitored by quantitative measurement of cells expressing endothelial cell specific markers such as angiogenic factors, proteolytic enzymes and endothelial cell specific cell adhesion molecules.

The present invention also provides a "pharmaceutical composition", which is intended to include the combination of an extract of *Trapa natans L.* with at least one other substance, e.g. a carrier, stabilizer, preservative or another active agent, such as another therapeutic agent, making the composition suitable for diagnostic or therapeutic uses in vitro, in vivo or ex vivo. Examples of "another therapeutically active agent" include steroids, e.g. prednisone, prednisolone, methylprednisolone, hydrocortisone, cortisone, and dexamethasone, non-steroidal anti-inflammatory drugs, aurothiomalate, aurothioglucose, d-penicillamine, chloroquine, hydroxychloroquine, sulfasalazine, azathioprine, and anti-tumor agents, e.g. interferon alpha, interferon beta, interferon gamma, interleukin-2, aldesleukin, filgrastim, sargramostim, levamisole, BCG vaccine, methotrexate, 5-fluorouracil, floxuridine, cytarabine, 5-azacytidine, mercaptopurine, thioguanine, pentastatin, fludarabine, cladribine, gemcitabine, mechlorethamine, chlorambucil, cyclophosphamide, melphalan, lomustine, carmustine, semustine, streptozocin, dacarbazine, busulfan, thiotepa, altretamine, ifosfamide, cisplatin, carboplatin, procarbazine, actinomycin D, plicamycin, bleomycin, doxorubicin, daunorubicin, idarubicin, mitoxanthrone, mitomycin, vincristine, vinblastine, vinorelbine, etoposide, teniposide, paclitaxel, topotecan, asparaginase, hydroxyurea, mitotane, dexamethasone, aminoglutethimide, estradiol, diethylstilbestrol, hydroxyprogesterone, medroxyprogesterone, megestrol, testosterone, fluoxymesterone, tamoxifen, leuprolide and flutamide.

As used herein, the term "pharmaceutically acceptable carrier" encompasses any standard pharmaceutical carriers, such as a phosphate buffered saline solution, water, preferably sterile water, emulsifiers and wetting agents. For examples of pharmaceutical carriers, stabilizers and adjuvants, see Martin, REMINGTON'S PHARM. SD., 15TH ED. (Mack Publ. Co., Easton (1975)).

An "effective amount" is an amount sufficient to effect the beneficial or desired result. For example, a therapeutic amount is one that achieves the desired therapeutic effect. A prophylactically effective amount is an amount necessary to prevent onset of disease or disease symptoms.

The present invention provides a method for inhibiting the pathological growth of endothelial cells by delivering to the cells a growth inhibitory amount of an extract of *Trapa natans L.* This invention also provides a method of inhibiting vascularization in a tissue by delivering to the tissue an anti-vascularization amount of an extract of *Trapa natans L.* These methods can be practiced in vitro or in vivo. When practiced in vitro, endothelial cells or vascularized tissue is cultured under conditions well known to persons skilled in the art, e.g., as exemplified below. The cells and/or tissue can be from an established cell line or cultured from a biopsy sample obtained from a subject. The cells and/or tissue is then exposed to an extract of *Trapa natans L.*, e.g. by adding the extract of *Trapa natans L.* to the culture medium of the cells and/or tissue.

According to the invention, an extract of *Trapa natans L.* is prepared by exposing *Trapa natans L.*, or portion thereof such as fruits, leaves, stems, branches, trunk, bark and roots, preferably meshed, crushed or ground, to an organic solvent or, preferably, an aqueous medium, and separating the resultant liquid from at least some, preferably substantially all, more preferably all, of the solid portion of *Trapa natans L.* to obtain an extract in the form of a liquid, which optionally can be reduced, e.g. by solvent evaporation or lyophilization, to a solid form after the removal of the organic solvent or water to obtain an extract in the form of a solid. The organic solvent, preferably, is a polar organic solvent, e.g. an alcohol such as methanol, ethanol, n-propanol, isopropanol, n-butanol, isobutanol and tert-butanol, with methanol or ethanol preferred. More preferably, in the preparation of the extract of *Trapa natans L.* of the invention, the fruit of *Trapa natans L.*, or portion of the fruit, is used as one of the starting materials, so the fruit (fresh or dry two-horned fruit or four-horned fruit, or a mixture thereof), or portion thereof, is exposed to the aqueous medium or organic solvent and separating, e.g. by centrifugation or filtration, the resultant liquid from the solid portion of the *Trapa natans L.* fruit to obtain the extract. Further more preferably, the shell of the fruit of *Trapa natans L.* is separated from the pulp, and then the shell, or portion thereof, is meshed, crushed or ground before being exposed to the aqueous medium or organic solvent. Optionally, the extract of *Trapa natans L.* of the invention can be prepared by exposing *Trapa natans L.*, or portion thereof such as the shell of the fruit, optionally meshed, crushed or ground, to an organic solvent or, preferably, aqueous medium, separating the resultant liquid from the solid portion of *Trapa natans L.* to form a liquid and removing, e.g. via dialysis, ultrafiltration or chromatography, compounds having a molecular weight of about 150 to about 3500, preferably about 150 to about 2000, more preferably about 150 to about 1000, further more preferably about 170 to about 600, even more preferably about 170 to about 400, much more preferably about 170 to about 300, most preferably about 170 to about 200, from the liquid to obtain an extract in a liquid form, which optionally can be reduced to a solid form after the removal of the organic solvent or water to obtain an extract in the form of a solid. Within the scope of the invention are embodiments of the extract of *Trapa natans L.* containing no gallic acid.

The invention also provides a method of inhibiting the growth of tumor cells, preferably cancer cells, comprising exposing the tumor cells to an effective amount of an extract of *Trapa natans L.* containing no (a) compounds having a molecular weight of about 150 to about 3500, preferably about 150 to about 2000, more preferably about 150 to about 1000, further more preferably about 170 to about 600, even more preferably about 170 to about 400, much more preferably about 170 to about 300, most preferably about 170 to about 200, or (b) no gallic acid and/or derivatives of gallic acid such as alkylated or hydroxylated gallic acids.

Not every therapy is effective for each individual and therefore, an in vitro assay to gauge efficacy for each subject would be advantageous. The present invention provides a method to determine whether therapy with an extract of *Trapa natans L.* will treat the subject's specific disease related to pathological proliferation of endothelial cells. For example, a tissue biopsy is isolated from the subject and contacted with an effective amount of an extract of *Trapa natans L.*, or a pharmaceutical composition containing the extract. Inhibition of pathological growth of endothelial cells as determined by conventional procedures, e.g., the CPAE assay described herein, indicates whether the *Trapa natans L.* extract or pharmaceutical composition comprising the extract would be effective in treating the subject.

This invention also provides a method of treating a disorder associated with pathological neovascularization in a subject by administering to the subject a therapeutically effective amount of an extract of *Trapa natans L.*, or a pharmaceutical composition containing the extract. As used in this context, to "treat" means to alleviate the symptoms associated with pathological neovascularization as well as the reduction of neovascularization. Such disorder includes, but is not limited to arthritic conditions, neovascular-based dermatological conditions, diabetic retinopathy, restinosis, Karposi's sarcoma, age-related macular degeneration, telangectasia, glaucoma, keloids, corneal graft rejection, wound granularization, angiofibroma, Osler-Webber Syndrome, myocardial angiogenesis, psoriasis, scleroderma, and inflammatory disorders such as hemorrhoids caused by or associated with pathological angiogenesis or neovascularization. Exemplary arthritic conditions are rheumatoid arthritis and osteoarthritis.

The invention also provides a method of preventing or inhibiting, e.g. stopping, reducing, slowing or delaying, cancer metastasis comprising administering an extract of *Trapa natans L.* to a subject having cancer, wherein the subject is in need of prevention or inhibition of cancer metastasis. Administration of the extract of *Trapa natans L.* for the treatment of arthritic conditions will result in decreased blood vessel formation in cartilage, specifically joints, resulting in increased mobility and flexibility in these regions. For the treatment of psoriasis, administration of the extract of *Trapa natans L.* will reduce dermatological symptoms such as scabbing, flaking and visible blood vessels under the surface of the skin. In diabetic retinopathy, administration of the extract of *Trapa natans L.* will reduce the formation of extraneous blood vessels in the retina, resulting in unobstructed vision. In the treatment of Kaposi's sarcoma, administration of the extract of *Trapa natans L.* will inhibit the growth and/or further formation of blood vessels, thereby inhibiting the formation of lesions.

The extracts of *Trapa natans L.* can be delivered orally, buccally, nasally, rectally, intravenously, intraperitoneally, intramuscularly, topically such as transdermally or ophthalmologically, vaginally or via inhalation. When the extracts of *Trapa natans L.* are administered to subjects such as humans, e.g. human patients, or other mammals such as mice, rats, horses, pigs, sheep or cattle, the extracts can be mixed with a pharmaceutically acceptable carrier and then administered. Therapeutic amounts of the extracts of *Trapa natans L.* can be empirically determined by a person skilled in the art and will vary with the disorder being treated, the pathology involved, the type of cells being targeted, and the subject being treated. The therapeutic amounts of the extracts of *Trapa natans L.* can vary between 0.1 mg/day to 1 g/day, preferably 1 mg/day to 500 mg/day, more preferably 10 mg/day to 100 mg/day. Administration in vivo can be effected in one dose, continuously or intermittently throughout the course of treatment.

The pharmaceutical compositions may take the form of tablets, lozenges, granules, capsules, pills, ampoules, suppositories or aerosol form. They may also take the form of suspensions, solutions and emulsions of the active ingredient in aqueous or non-aqueous diluent, syrups, granulates or powders.

While it is possible for an extract of *Trapa natans L.* to be administered alone, it can also be presented in a pharmaceutical formulation comprising the extract of *Trapa natans L.* together with one or more pharmaceutically acceptable carriers and optionally other therapeutic agents. Each carrier must be "acceptable" in the sense of being compatible with the other ingredients of the formulation and not injurious to the subject such as a patient.

The pharmaceutical formulation may conveniently be presented in unit dosage form and may be prepared by bringing into association the extract of *Trapa natans L.* liquid carriers or finely divided solid carriers or both, and then if necessary shaping the product.

Formulations of the present invention suitable for oral administration may be presented as discrete units such as capsules, cachets or tablets, each containing a predetermined amount of the extract of *Trapa natans L.*; as a powder or granules; as a solution or suspension in an aqueous or non-aqueous liquid; or as an oil-in-water liquid emulsion or a water-in-oil liquid emulsion. The extract of *Trapa natans L.* may also be presented a bolus, electuary or paste.

A tablet may be made by compression or molding of an extract of *Trapa natans L.*, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising an extract of *Trapa natans L.* in an inert basis such as gelatin and glycerin, or sucrose and acacia; and mouthwashes comprising the extract of *Trapa natans L.* in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with the extract of *Trapa natans L.* and optionally one or more excipients or diluents.

Some of the embodiments of the pharmaceutical formulations can be applied as a topical ointment or cream containing the extract of *Trapa natans L.* When formulated in an ointment, the extract may be employed with either a paraffinic or a water miscible ointment base. Alternatively, the ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound, which enhances absorption or penetration of the extract of *Trapa natans L.* through the skin or other affected areas. Examples of such dermal penetration enhancers include dimethylsulfoxide and related analogues.

The oily phase of the emulsions of this invention may be constituted from known ingredients in any known manner. While this phase may comprise merely an emulsifier (otherwise known as an emulgent), it desirably comprises a mixture of at lease one emulsifier with a fat or oil or with both a fat and oil. Preferably, a hydrophilic emulsifier is included together with a lipophilic emulsifier, which acts as a stabilizer. It is also preferred to include both oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, and glycerol monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing the extract of Trapa natans L. and one or more appropriate carriers.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the extract of Trapa natans L.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the extract of Trapa natans L. to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In addition to the ingredients particularly mentioned above, the formulations of this invention may include other agents conventional in the art having regard to the type of formulation in question, for example, those suitable of oral administration may include such further agents as sweeteners, thickeners and flavoring agents.

The extracts of Trapa natans L. and compositions containing one or more of the extracts may also be presented for the use in the form of veterinary formulations, which may be prepared, for example, by methods that are conventional in the art.

This invention further provides a method for screening for a therapeutic agent for inhibiting neovascularization or endothelial cell growth. The screen requires:

(a) contacting a test agent with a suitable cell or tissue sample;

(b) contacting a separate sample of the suitable cell or tissue sample with a therapeutically effective amount of an extract of Trapa natans L., and thereafter (c) comparing the growth of endothelial cells in the sample of step (a) with the growth of endothelial cells in the sample of step (b), and wherein any test agent of step (a) that inhibits the endothelial cell growth to the same or similar extent as the sample of step (b) is useful as a therapeutic agent for inhibiting neovascularization or the pathological growth of endothelial cells.

EXAMPLE 1

Inhibition of Endothelial Cell Proliferation by Extract of Trapa natans L.

Preparation of the Extract of Trapa natans L.

The shells of two-horned and four-horned fruit of Trapa natans L. were separated from the pulp. The separated shells were ground to pieces of about 2 mm in size by crushing the shells with a mortar and pestle after they had been frozen with liquid nitrogen. Twenty grams of the ground shells were exposed to double distilled water having a volume 5 times to 10 times that of the ground shells for 2 to 4 hours at 80°-100° C. (optionally, at lower than 80° C., such as 4° C. or 20° to 25° C., for 4 to 12 hours instead) with stirring to obtain a mixture. The mixture was then filtered through two layers of Miracloth to remove solid residues. The turbid filtrate was clarified by centrifugation at about 1,500 rpm at room temperature. The supernatant was decanted from the sediment to obtain a clear brown solution, which could be used as an extract of Trapa natans L. of the invention. However, in this experiment, the clear brown solution was lyophilyzed to form a lyophilized crude extract for storage. The lyophilized crude extract was later dissolved in 10 ml double distilled water, and dialyzed overnight in a dialysis tubing with a cutoff of 1,000 MW with three changes of 250 ml double distilled water. The liquid inside the dialysis tubing became one form of the extract of Trapa natans L. (TE), which was subjected to biological assays below.

Endothelial Cell Assays

The solid form of the extract of Trapa natans L. (TE) prepared above was used in an endothelial cell assay (CPAE) carried out according to the procedures of Connally et al. (1986) Anal. Biochem. 152:136-140 with modifications (Liang and Wong (2000), "Angiogenesis: From the Molecular to Integrative Pharmacology", edited by Maragoudakis, Kluwer Academic/Plenum Publishers, New York, pp 209-223). At a concentration of 100 ug/ml, the solid form of the extract of Trapa natans L. (TE) inhibited the proliferation of the endothelial cells by 86.75%.

EXAMPLE 2

Inhibition of Cancer Cell Growth by Extract of Trapa natans L.

The solid form of the extract of Trapa natans L. (TE) prepared in Example 1 was used in cancer cell proliferation assays to determine the effects of the extract on the growth of three types of cancer cells (Lncap, prostate cancer cells; SW 480, colorectal cancer cells; and HTB 72, melanoma cells) by exposing the cancer cells to the solid form of the extract at 100 ug/ml in vitro and measuring the proliferation of the cancer cells. For comparison purposes, the effects of two anticancer drugs, cisplatin and paclitaxel, on the growth of the three types of cancel cells were also determined in vitro. The results of the bioassays are presented in Table I, which demonstrates that the addition of the extract of Trapa natans L. to the cancer cell cultures led to significant inhibition of the growth of cancer cells.

| Agent | Inhibition, % | | |
|---|---|---|---|
| | Lncap | SW 480 | HTB 72 |
| TE* | 74.67 | 76.18 | 27.31 |
| Cisplatin** | 94.91 | 78.25 | 93.78 |
| Paclitaxel** | 57.98 | 0.0 | 22.61 |

*100 ug/ml of cell media
**50 ul saturated solution in 1 ml of cell media

EXAMPLE 3

Different concentrations of the lyophilized crude extract of *Trapa natans L.*, the dialyzed extract of *Trapa natans L.* (TE), i.e. the liquid inside the dialysis tubing with a cutoff of 1000 M.W., and the water outside the dialysis tubing obtained in Example 1 were used in the endothelial cell assay. The results are presented in FIG. 1, which shows that the lyophilized crude extract of *Trapa natans L.* and the dialyzed extract of *Trapa natans L.* (TE) inhibited the growth of the endothelial cells in a concentration-dependent fashion. In contrast, the water outside the dialysis tubing did not significantly inhibit the proliferation of the endothelial cells. The data proved that the extract of *Trapa natans L.* was an extremely effective endothelial cell growth inhibitor. Since the anti-angiogenic component(s) of the extract of *Trapa natans L.* was retained inside the dialysis tubing, the anti-angiogenic component(s) was not a low molecular weight substance.

EXAMPLE 4

The lyophilized crude extract of *Trapa natans L.* prepared in Example 1 was dissolved in double distilled water and dialyzed overnight in a dialysis tubing with a cutoff of 3,500 MW with three changes of double distilled water. The liquid, i.e. the dialyzed extract, inside the dialysis tubing was shown to inhibit the proliferation of endothelial cells in an endothelial cell assay. This experiment demonstrated that the anti-angiogenic component(s) of the extract of *Trapa natans L.* had a molecular weight of at least about 3,500.

EXAMPLE 5

As an example of an animal model for determining the therapeutic amount of an extract of *Trapa natans L.*, groups of nude mice (Balb/c NCR nu/nu female, Simonsen, Gilroy, Calif.) are each subcutaneously inoculated with about $10^5$ to about $10^9$ hyperproliferative cells as defined herein. When the graft is established, the extract is administered, for example, by subcutaneous injection around the graft. Measurements to determine reduction of graft size are made in two dimensions using venier calipers twice a week.

EXAMPLE 6

An example of animal models for determining the therapeutic effect of the extract of the invention in treating arthritic conditions is presented herein. The MRL/lpr mice (MRL/MpJ-Fas$^{lpr}$) from Jackson Labs, Maine are useful to test or monitor efficacy of treating arthritic conditions with an extract of *Trapa natans L.* of the invention. After the mice are administered with the extract, reduced swelling of the joints and hind legs of animals and reduced cartilage degradation that can be monitored by X-ray are indicative of the positive therapeutic effect of the extract in treating arthritic conditions.

EXAMPLE 7

Another example of animal models for determining the therapeutic effect of the extract of the invention in treating arthritic conditions is presented herein. Groups of Lewis rats (age 8 weeks, 130-150 g, Jackson Labs, Maine, USA) are immunized with bovine type II (BII) collagen to induce arthritic conditions. BII is dissolved in 0.1 M acetic acid at 400 ug/ml. Each rat is injected intradermally with 20 ug (100 ul) of an emulsion of equal volumes of BII and ICFA (incomplete Freund's adjuvant) at the base of the tail. When arthritic conditions are established, an extract of *Trapa natans L.* of the invention is administered to the rats and observations on a four-point scale are made on a variety of induced physical ailments over a period of 28 days to show that the extract is effective in treating arthritic conditions.

What is claimed is:

1. A method for inhibiting metastasis of cancer in a subject suffering from cancer, comprising administering a cancer metastasis inhibitory effective amount of a product comprising an extract from the shells of two-horned and four-horned fruits of *Trapa natans L.* to the subject, wherein the cancer is cancer of the colon, lung, liver, kidney, prostate, breast and/or cervix.

2. The method of claim 1, wherein the extract is prepared by exposing the shells of two-horned and four-horned fruits of *Trapa natans L.* to a polar organic solvent or aqueous medium.

3. The method of claim 2, wherein the extract is prepared by exposing the shells of two-horned and four-horned fruits of *Trapa natans L.* to a polar organic solvent.

4. The method of claim 3, wherein the polar organic solvent is an alcohol.

5. The method of claim 2, wherein the extract is prepared by exposing the shells of two-horned and four-horned fruits of *Trapa natans L.* to an aqueous medium.

6. A method for inhibiting metastasis of cancer in a subject suffering from cancer, comprising administering a cancer metastasis inhibitory effective amount of a product comprising an extract from the shells of two-horned and four-horned fruits of *Trapa natans L.* to the subject, the extract containing (a) no compounds having a molecular weight of about 170 to about 200, or (b) no gallic acid and/or alkoxylated or hydroxylated gallic acid, wherein the cancer is cancer of the colon, lung, liver, kidney, prostate, breast and/or cervix.

7. The method of claim 1, wherein the subject is in need of inhibition of metastasis of the cancer.

8. The method of claim 1, wherein the subject is a mammal.

9. The method of claim 8, wherein the mammal is a human.

10. The method of claim 9, wherein the mammal is a human patient.

11. The method of claim 8, wherein the subject is a mammalian pet.

12. The method of claim 11, wherein the mammalian pet is a cat or dog.

13. The method of claim 11, wherein the subject is a mammalian farm animal.

14. The method of claim 1, further comprising applying an anti-cancer therapeutic regimen to the subject.

15. The method of claim 14, wherein the anti-cancer therapeutic regimen comprises the administration of at least one anti-cancer chemotherapeutic agent to the subject.

16. The method of claim 15, wherein the at least one anti-cancer chemotherapeutic agent is selected from the group consisting of doxorubicin, daunorubicin, epirubicin, paclitaxel, docetaxel, 5-fluorouracil, cyclophosphamide, methotrexate, cisplatin, carboplatin,. vincristine, vinblastine, etoposide, tenoposide, bleomycin, plicamycin, mitomycin, mitotane, tamoxifen, letrozole, anastrozole, exemestane, vinorelbine, gemcitabine, capecitabine and Avastin.

17. The method of claim 15, wherein the anti-cancer therapeutic regimen comprises administering to the subject at least one therapeutic agent selected from the group consisting of interferon alpha, interferon beta, interferon gamma, interleukin-2, aldesleukin, filgrastim, sargramostim, levamisole, BCG vaccine, methotrexate, 5-fluorouracil, floxuridine, cytarabine, 5-azacytidine, mercaptopurine, thioguanine, pentastatin, fludarabine, cladribine, gemcitabine, mechiorethamine, chlorambucil, cyclophosphamide, melphalan, lomustine, carmustine, semustine, streptozocin, dacarbazine, busulfan, thiotepa, altretamine, ifosfamide, cisplatin, carboplatin, procarbazine, actinomycin D, plicamycin, bleomycin, doxorubicin, daunorubicin, idarubicin, mitoxanthrone, mitomycin, vincristine, vinbiastine, vinorelbine, etoposide, teniposide, paclitaxel, topotecan, asparaginase, hydroxyurea, mitotane, dexamethasone, aminoglutethimide, estradiol, diethyistilbestrol, hydroxyprogesterone, medroxyprogesterone, megestrol, testosterone, fluoxymesterone, tamoxifen, leuprolide and flutamide.

18. The method of claim 14, wherein the anti-cancer therapeutic regimen comprises the administration of anti-cancer radiation to the subject.

19. The method of claim 1, further comprising the application of surgery in the subject.

20. The method of claim 1, further comprising administering to the subject at least one anti-angiogenesis agent other than the extract from the shells of the two-horned and four-horned fruits of *Trapa natans L.*

21. The method of claim 20, wherein the at least one anti-angiogenesis agent other than the extract from the shells of two-horned and four horned fruits of *Trapa natans L.* is selected from the group consisting of Avastin, ammonium sulfate precipitate of shark cartilage, extracts of shark cartilage, Shimeji DEAB alpha, Shimeji Mono-Q alpha, 3-aminobenzamide, cisplatin, dalteparin, suramin, 2-methoxyestradiol, thalidomide, combretastain A4 phosphate, genistein, interferon-alpha, VEGF-Trap, celecoxib, halofuginone hydrobromide and interleukin-12.

22. The method of claim 21, wherein the at least one anti-angiogenesis agent other than the extract from the shells of the two-horned and four-horned fruits of *Trapa natans L.* is Avastin.

23. The method of claim 6, wherein the extract is prepared by exposing the shells of the two-horned and four-horned fruit of *Trapa natans L.* to an alcohol or aqueous medium.

24. The method of claim 6, further comprising applying an anti-cancer therapeutic regimen to the subject.

25. A method for inhibiting metastasis of cancer in a subject suffering from cancer, comprising administering a cancer metastasis inhibitory effective amount of a product consisting essentially of an extract from the shells of the two-horned and four-horned fruits of *Trapa natans L.* to the subject, wherein the cancer is cancer of the colon, lung, liver, kidney, prostate, breast and/or cervix.

26. The method of claim 25, wherein the extract is prepared by exposing the shells of the two-horned and four-horned fruits of Trapa natans L. to an alcohol or aqueous medium.

27. The method of claim 25, further comprising applying an anti-cancer therapeutic regimen to the subject.

\* \* \* \* \*